United States Patent [19]

Giller et al.

[11] 4,052,419

[45] Oct. 4, 1977

[54] METHOD OF PREPARING 5-NITROFURFURAL DIACETATE

[76] Inventors: Solomon Aronovich Giller, ulitsa Pernavas, 10, kv. 76; Karl Karlovich Venter, ulitsa Sporta, 7, kv. 10; Margarita Aldonovna Trushule, ulitsa Katrindambis, 22-D, kv. 10; Guntis Erikovich Berggrin, ulitsa Pernavas, 57, kv. 10; Robert Avgustovich Brinkmanis, ulitsa Brivzemnieka, 22, kv. 4, all of Riga; Uldis Yanovich Mikstais, ulitsa Elgavas, 4, kv. 64; Paul Alexandrovich Stankevich, ulitsa Mendeleeva, 20, kv. 84, both of Olaine, all of U.S.S.R.

[21] Appl. No.: 580,900

[22] Filed: May 27, 1975

[51] Int. Cl.$^2$ .......................................... C07D 307/71
[52] U.S. Cl. .................................................. 260/347.4
[58] Field of Search .................................... 260/347.4

[56] References Cited

U.S. PATENT DOCUMENTS 2,490,006  11/1949  Kimel et al. .................... 260/347.4

FOREIGN PATENT DOCUMENTS 1,347,092  11/1963  France ............................ 260/347.4
797,961   7/1958  United Kingdom .............. 260/347.4

OTHER PUBLICATIONS

Wagner et al., Synthetic Organic Chem., New York, John Wiley Inc., (1959), pp. 746-748.

*Primary Examiner*—Henry R. Jiles
*Assistant Examiner*—Bernard Dentz
*Attorney, Agent, or Firm*—Fleit & Jacobson

[57] ABSTRACT

A method of preparing 5-nitrofurfural diacetate which comprises nitration furfural or furfural diacetate at a temperature within the range of from $-10°$ to $+10°$ C; said nitration being effected by the gradual simultaneous addition of furfural or a furfural diacetate solution in acetic anhydride and a mixture of nitric and sulphuric acids into acetic anhydride at a temperature within the range of from $-10°$ to $+10°$ C under continuous stirring of the reaction mixture. In doing so, molar proportions of furfural or furfural diacetate and nitric acid and sulphuric acid are maintained equal to 1:1.1–2:0.036–0.041 respectively and said compounds are added into acetic anhydride at such rates as to maintain the nitration reaction temperature at a predetermined level. The reaction mixture resulting from the nitration is treated with water at a weight ratio between water and the starting acetic anhydride ranging from 1.1:1 to 1.8:1 respectively and at a temperature within the range of from 0° to 15° C; the reaction mixture is then neutralized with an alkali to a pH = 3.5 – 5 at a temperature within the range of from 0° to 25° C, maintained at a temperature of from 45° to 55° C, and the desired product is thereafter isolated from said reaction mixture.

9 Claims, 1 Drawing Figure

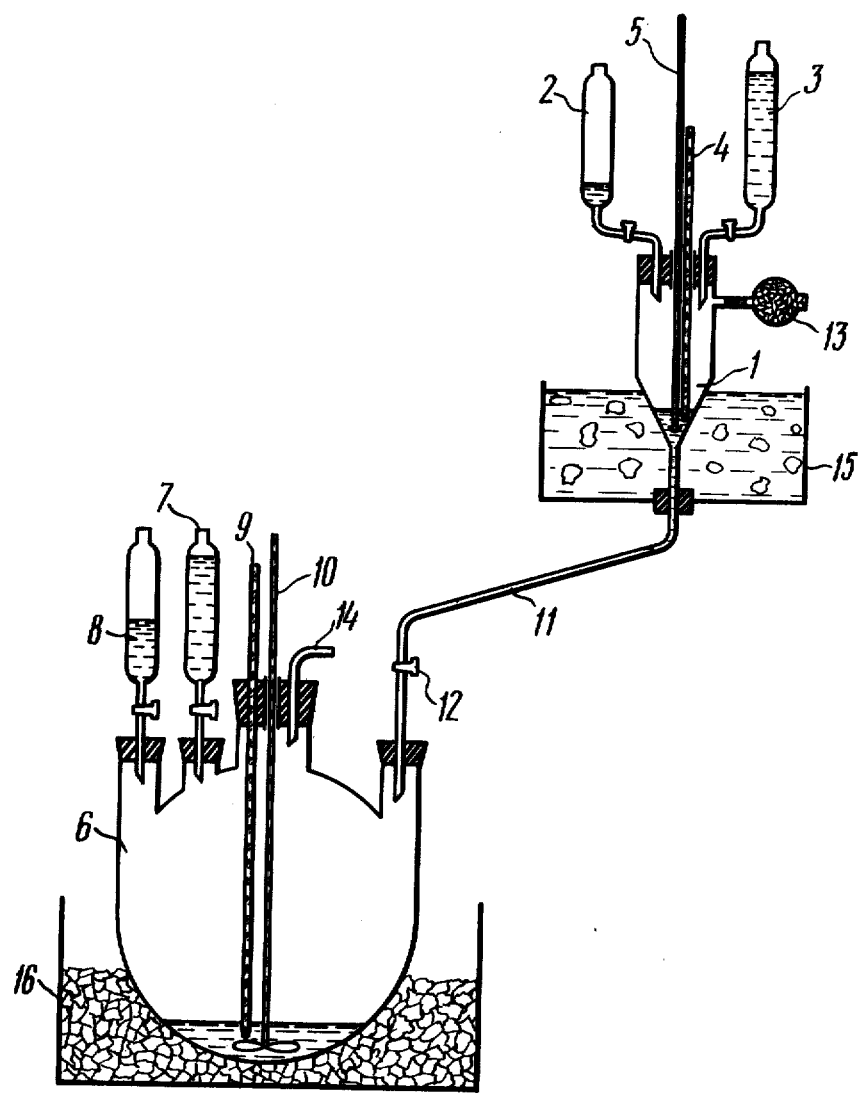

METHOD OF PREPARING 5-NITROFURFURAL DIACETATE

The present invention relates to methods of preparing 5-nitrofurfural diacetate by nitration of furfural or furfural diacetate in the presence of acetic anhydride. 5-Nitrofurfural diacetate is a starting raw material for the production of chemical therapeutical compositions which find an extensive use in medicine and agriculture.

Known in the art are some methods of preparing 5-nitrofurfural diacetate by nitration of furfural or furfural diacetate in the presence of acetic anhydride, which methods consist of the following steps:

a. preparation of a solution of acetyl nitrate in an excess of acetic anhydride by adding nitric acid to acetic anhydride under stirring and external cooling. Said acetyl nitrate solution is prepared at a temperature within the range of from $-10°$ to $+40°$ C and the following reaction occur therewith:

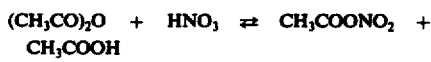

b. nitration of furfural or furfural diacetate by adding furfural or a solution of furfural diacetate in acetic anhydride to the solution of acetyl nitrate prepared in the step (a). The nitration of furfural or furfural diacetate is effected at a temperature within the range of from $-10°$ to $+42°$ C, with 1.2 to 2 moles of the starting nitric acid and 2.5 to 7.6 moles of acetic anhydride per mole of furfural or furfural diacetate being employed.

The preparation of the acetyl nitrate solution and nitration of furfural or furfural diacetate may be effected in the presence of catalysts such as concentrated sulphuric acid, para-toluene sulphonic acid, and the like, and c. treatment of the reaction mixture from step (b) containing an intermediate nitration product with cold water at a weight ratio between water and the starting acetic anhydride ranging from 0.75:1 to 1.5:1 respectively and at a temperature within the range of from 0° to 25° C to decompose the acetic anhydride excess and acetyl nitrate; neutralization of the reaction mixture with an alkali to a pH ranging from 1.8 to 7 at a temperature within the range of from 0° to 50° C; maintaining the reaction mixture at a temperature within the range of from 50° to 80° C to convert the intermediate nitration product into the desired product; and isolation of the latter from the reaction mixture by crystallization upon cooling.

All the above-mentioned prior art methods have a disadvantage residing in a potential hazard of the stages dealing with the preparation of the acetyl nitrate solution and nitration of furfural or furfural diacetate, since in the first stage of the synthesis, after intermixing nitric acid and acetic anhydride, a relatively large amount of a hazardous and instable acetyl nitrate is accumulated in the reactor.

In the paper by T. A. Brown, J. A. C. Watt, Chemistry in Britain, 1967, 3, 504, it is noted that manipulations with a solution of acetyl nitrate in acetic anhydride prepared in accordance with the above-described method resulted in several grave casualties which took place due to the hazardous nature of this solution; data illustrating its explosive properties are given in the following Table 1.

Table 1

| Amount of the starting nitric acid in a mixture with acetic anhydride, per cent | Properties of the prepared solution of acetyl nitrate in acetic anhydride |
|---|---|
| 26 | does not detonate |
| 41 | " |
| 50 | " |
| 55 | detonates |
| 60 | " |
| 70 | " |

In the practice of this method, use is made, for safety purposes, of strongly diluted acetyl nitrate solutions in acetic anhydride. This, however, results in an increased consumption of great amounts of rather expensive acetic anhydride, whereby production costs of 5-nitrofurfural diacetate are substantially increased.

Moreover, our investigations have shown that in the case of a prolonged period of storage of such acetyl nitrate solution at a temperature above 0° C (which takes place in commercial production), nitrating ability thereof is substantially impaired. This may be attributed to the fact that the composition of said solution is changed with time due to undesirable side reactions (during storage of the acetyl nitrate solution in acetic anhydride, the content of the nitrating agent, i.e. acetyl nitrate, in the solution is decreased, while concentration of nitrogen oxides is increased). Thus, in the nitration of furfural with a preliminary natured acetyl nitrate solution in acetic anhydride in the presence of a catalyst, i.e. sulphuric acid, a reduced yield of 5-nitrofurfural diacetate and impaired quality thereof are observed. Dependence of yields and quality of the desired 5-nitrofurfural diacetate on the time of the acetyl nitrate solution keeping in acetic anhydride is shown in Table 2 hereinbelow. Therewith, the nitration conditions were as follows: nitration temperature $-5°$ C; molar ratios between furfural, starting nitric acid (specific gravity 1.5), concentrated sulphuric acid (specific gravity 1.84) and acetic anhydride were 1:1.3:0.036:6.5 respectively).

Table 2

| Duration of preliminary ageing of the acetyl nitrate solution in acetic anhydride at 15–20° C temperature, hours | 5-nitrofurfural diacetate | |
|---|---|---|
| | Yield, % | Melting point, ° C |
| 0 | 71.5 | 90 – 92 |
| 1 | 60.7 | 90 – 92 |
| 3 | 40.2 | 87 – 90 |
| 6 | 17.0 | 80 – 85 |
| 24 | 0 | — |

In a similar manner, the yield of 5-nitrofurfural diacetate is reduced in the case of nitrating furfural diacetate which is evidenced by the data given in Table 3 hereinbelow. The nitration conditions in this case were as follows: nitration temperature $-5°$ C; molar proportions of furfural diacetate, starting nitric acid (specific gravity 1.5), concentrated sulphuric acid (specific gravity 1.84) and acetic anhydride were 1:2:0.036:8.8 respectively.

Table 3

| Duration of preliminary ageing of the acetyl nitrate solution in acetic anhydride at 15–20° C temperature, hours | 5-nitrofurfural diacetate | |
|---|---|---|
| | Yield, % | Melting point, ° C |
| 0 | 75.2 | 90 – 92 |
| 1 | 70.2 | 90 – 91 |
| 3 | 44.9 | 90 – 91 |

Table 3-continued

| Duration of preliminary ageing of the acetyl nitrate solution in acetic anhydride at 15-20° C temperature, hours | 5-nitrofurfural diacetate | |
|---|---|---|
| | Yield, % | Melting point, °C |
| 6 | 42.3 | 90 - 91 |

It is an object of the present invention to provide an improved method of preparing 5-nitrofurfural diacetate which would ensure nitration of furfural or furfural diacetate under non-hazard conditions.

It is another object of the present invention to provide such a method which would make it possible to prepare 5-nitrofurfural diacetate with a high yield and good quality.

Still another object of the present invention is to provide a method which would make it possible to reduce the acetic anhydride consumption.

These and other objects of the present invention are accomplished by a method of preparing 5-nitrofurfural diacetate which involves the use of furfural or a solution of furfural diacetate in acetic anhydride, acetic anhydride, a mixture of nitric and sulphuric acids and comprises nitration of furfural or furfural diacetate at a temperature of from −10° to +10° C in the presence of acetic anhydride and a catalyst, i.e. sulphuric acid, to give a reaction mixture, followed by treating this reaction mixture with water at a weight ratio between water and starting acetic anhydride ranging from 1:1.1 to 1.8:1 respectively and at a temperature ranging from 0° to 15° C, neutralizing the reaction mixture with an alkali to a pH of 3.5 to 5 at a temperature within the range of from 0° to 25° C, maintaining said mixture at a temperature within the range of from 45° to 55° C, and isolation of the desired product from said reaction mixture. In doing so, in accordance with the present invention, said nitration of furfural or furfural diacetate is effected by simultaneously and gradually adding furfural or a furfural diacetate solution in acetic anhydride and a mixture of nitric acid and sulphuric acid into acetic anhydride having a temperature ranging from −10° to +10° C and with constantly stirring said reaction mixture; with, molar ratios between furfural or furfural diacetate and nitric and sulphuric acids being maintained equal to 1:1.1–2:0.036–0.041 respectively and said reagents are introduced into acetic anhydride at such rates as to maintain the nitration reaction temperature at a predetermined value.

It is advisable that the nitration reaction be effected at a molar ratio of furfural or furfural diacetate and acetic anhydride equal to 1:2.5–6.3 respectively.

In the method according to the present invention, furfural may be also added into acetic anhydride in the form of its solution in acetic anhydride.

In order to reduce consumption of acetic anhydride, it is advisable that the nitration of furfural or furfural diacetate be effected by adding furfural or its solution in acetic anhydride or a solution of furfural diacetate in acetic anhydride as well as a mixture of nitric and sulphuric acids into a mixture of acetic anhydride with an inert chlorine-containing organic solvent at a volumetric ratio of acetic anhydride and said solvent ranging from 1:1.4 to 1:2 respectively. In such an embodiment of the nitration process, after neutralization of the reaction mixture with an alkali and prior to its maintaining at a temperature within the range of from 45° to 55° C, it is necessary, in order to ensure uniformity of the reaction mixture, to add, into the latter, a water-miscible organic solvent.

To improve conditions for the formation of the desired product, it is advantageous to distill-off said inert chlorine-containing organic solvent from the reaction mixture prior to the adding, into the latter, of said water-miscible organic solvent.

In the method of the present invention, as the inert chlorine-containing organic solvent, it is advisable to employ dicloromethane or carbon tetrachloride; as the water-miscible organic solvent use may be preferably made of ethanol, isopropanol, tetrahydrofuran or acetone.

The process of nitration of furfural or furfural diacetate in the method according to the present invention may be effected either periodically or continuously, i.e. without or with a continuous discharge of the resulting reaction mixture from the nitration zone. Examples 1–4, 6–8 given hereinbelow illustrate a periodically-operating embodiment of the nitration process; Example 5 shows a continuous scheme of the nitration process.

The method of preparing 5-nitrofurfural diacetate in accordance with the present invention ensures non-hazardous character of the nitration of furfural or furfural diacetate (in said method there is no accumulation or storing of any substantial amounts of hazardous acetyl nitrate). The method of the present invention makes it possible to reduce the consumption of acetic anhydride as well as to prepare the desired product with a high yield (ranging from 76 to 85% of the theoretical value) and a good quality (melting point of the product is 90°–92° C). No complicated equipment is required to perform the method of the present invention. It may be effected in conventional reactors provided with a mechanical stirrer and cooling-heating means.

The method according to the present invention is effected in the following manner.

Into acetic anhydride cooled to a temperature within the range of from −10° to +10° C furfural or its solution in acetic anhydride or a solution of furfural diacetate in acetic anhydride and a mixture of nitric acid and sulphuric acid are added gradually and simultaneously under constant stirring of the reaction mixture. It is necessary to effect a strictly proportional supply of the reagents so that molar ratios between furfural or furfural diacetate with sulphuric and nitric acids be maintained within the range of from 1:1.1 to 2:0.036–0.041 respectively. These compounds are added to the acetic anhydride at such rates as to ensure, by means of heat removal, the nitration temperature within the range of from −10° to +10° C. It is advisable that the nitration be effected at a molar ratio between furfural or furfural diacetate and acetic anhydride within the range of 1:2.5–6.3 respectively.

As has been mentioned hereinbefore, nitration of furfural or furfural diacetate may be performed either continuously or periodically.

As a result of the nitration process a reaction mixture is obtained containing an intermediate nitration product, viz. 5-nitro-2-acetoxy-2,5-dihydrofurfural diacetate. This reaction mixture is treated under stirring with water, to decompose an excess of acetic anhydride, at a temperature within the range of preferably from 2° to 4° C and at a weight ratio between water and the starting acetic anhydride ranging from 1.1:1 to 1.8:1 respectively. To effect said treatment, water may be used as a liquid or as ice. The water-treatment of the reaction mixture is effected at a temperature within the range of from 0° to 15° C, the temperature is maintained by heat removal.

To convert the above-mentioned intermediate nitration product contained in the reaction mixture, into the desired product, the reaction mixture should be neutralized with an alkali at a temperature within the range of from 0° to 25° C to a pH = 3.5 - 5 and then maintained at a temperature of from 50° to 55° C.

The treatment of the reaction mixture with water and neutralization with an alkali may be effected successively (first water-treatment and then neutralization) or simultaneously.

After all said operations, 5-nitrofurfural is isolated from the reaction mixture by may conventional technique such as by crystallization upon cooling.

The nitration process may be performed in such a manner when furfural or its solution in acetic anhydride or a solution of furfural diacetate in acetic anhydride as well as a mixture of nitric and sulphuric acids are added into a mixture of acetic anhydride with an inert chlorine-containing organic solvent such as dichloromethane or carbon tetrachloride. This technique ensures a minimal excess of acetic anhydride in the nitration of furfural or furfural diacetate, whereby the consumption of this rather expensive reagent is reduced and precipitation of nitration products as a solid precipitate hindering the reaction mixture stirring is avoided.

When inert chlorine-containing organic solvents are employed in the nitration process, the reaction mixture should have added to it, after its neutralization and prior to maintaining at a temperature of 45° - 55° C, organic solvents miscible with water such as ethanol, isopropanol, acetone or tetrahydrofurane. Addition of said solvents ensures that the resulting reaction mixture is homogeneous which contributes to more efficient conversion of the intermediate nitration product into the desired product.

Since this conversion of the intermediate nitration product into the desired product in the presence of inert chlorinated organic solvents, as a rule, immiscible with water proceeds rather slow, it is advisable to distill-off the inert chlorinated organic solvent from the reaction mixture prior to the addition thereto of a water-miscible organic solvent.

For better understanding of the present invention, the following Examples illustrating the preparation of 5-nitrofurfural diacetate are given hereinbelow.

EXAMPLE 1

To effect the nitration process, into 17.5 g (0.171M) of acetic anhydride at a temperature of 0°-(−5° C) added dropwise, under constant stirring, are at a time 3.24 g (0.034M) of furfural and a mixture of 2.8 g (0.044M) of fuming nitric acid (d = 1.51) and 0.12 g (0.0012M) of sulphuric acid (d = 1.84). Strict proportionality of simultaneous addition of said components should be ensured (prevailing amount of furfural added into acetic anhydride is not permitted). The reaction mixture temperature is maintained within the range of from 0° to −5° C by means of heat removal. Furfural and the mixture of nitric and sulphuric acids are added into acetic anhydride at such rates as to maintain the nitration temperature at the above-mentioned value.

When all the amount of furfural and the mixture of nitric and sulphuric acids is added into acetic anhydride, the reaction mixture is stirred at a temperature of from 0° to −5° C for additional 20 minutes and then poured onto 20 g of crushed ice and stirred for 30 minutes maintaining the reaction mixture temperature at 10°-15° C. The temperature within this range is maintained by means of external heat removal. Then the reaction mixture is added with 6.3 ml of a 25% aqueous solution of caustic soda (d = 1.27) under stirring to bring a pH value to 3.5 - 4.5; the reaction mixture temperature ranges from 15° to 25° C. The reaction mixture with said pH value is heated to a temperature of 50°-55° C and maintained at this temperature for 1 hour under stirring. Then, to isolate the desired product, the reaction mixture is cooled to a temperature 10°-15° C and stirred at this temperature for 2 hours. The resulting crystalline precipitate is filtered off, washed with cold water and dried at room temperature by means of phosphorus pentoxide. The yield of 5-nitrofurfural diacetate is 6.6 g (80.2% of the theoretical value as calculated on the amount of furfural introduced into the reaction); melting point of the product is 90°-92° C.

EXAMPLE 2.

Nitration of 2.4 g (0.025M) of furfural with a mixture of 2.0 g (0.032M) of fuming nitric acid and 0.1 g (0.001M) sulphuric acid in 7.7 g (0.075M) of acetic anhydride is effected in accordance with the procedure of Example 1. The remaining stages — treatment of the resulting reaction mixture with crushed ice and alkali, and isolation of the desired product are performed also in a manner similar to that of Example 1. The difference resides only in that the crushed ice is used in the amount of 11 g and a 25% aqueous solution of caustic soda is used in the amount of 3.1 ml. The yield of 5-nitrofurfural diacetate is 4.8 g (78.8% of the theoretical value); melting point of the product is 90° - 92° C.

EXAMPLE 3

Nitration of 2.4 g (0.025M) of furfural with a mixture of 2.0 g (0.032M) of fuming nitric acid and 0.1 g (0.001M) of sulphuric acid in 10.2 g (0.1M) of acetic anhydride is effected in a manner similar to that of Example 1. Molar proportions of furfural, nitric acid, sulphuric acid and acetic anhydride are 1:1.3:0.041:4 respectively.

After nitration, the resulting reaction mixture is poured onto 15 g of crushed ice and mixed for 30 minutes maintaining the reaction mixture temperature within the range of from 10° to 15° C. Thereafter, to the reaction mixture is added, under stirring, 4.1 ml of a 25% aqueous solution of caustic soda to bring the pH value to about 4, the reaction mixture temperature being 15°-25° C. The reaction mixture having the above-mentioned pH value is heated to a temperature of from 50° to 55° C and maintained at this temperature for 1 hour under stirring. The desired product isolation is effected in a manner similar to that of Example 1. The yield of 5-nitrofurfural diacetate is 4.9 g (81.4% of the theoretical value), the melting point of the desired product being 90°-91.5° C.

Effecting the nitration process in a manner similar to that described hereinabove but using different amounts of nitric acid, the following data were obtained illustrating yields and quality of 5-nitrofurfural diacetate these gates being shown in the following Table 4.

Table 4

| Molar ratios between furfural, nitric acid and acetic anhydride | 5-nitrofurfural diacetate | |
|---|---|---|
| | Yield, % | Melting point, ° C |
| 1:1.1:4 | 73.0 | 90–91 |
| 1:1.2:4 | 75.6 | 90–91 |

Table 4-continued

| Molar ratios between furfural, nitric acid and acetic anhydride | 5-nitrofurfural diacetate | |
|---|---|---|
| | Yield, % | Melting point, °C |
| 1:1.4:4 | 79.2 | 90–92 |
| 1:1.5:4 | 77.9 | 90–91 |
| 1:2.0:4 | 76.8 | 90–91 |

EXAMPLE 4

To perform a nitration process in 4.3 g (0.042M) of acetic anhydride at 0°– –10° C temperature, a solution of 5.0 g (0.025M) of furfural diacetate in 8.5 g (0.083M) of acetic anhydride and a mixture of 2.3 g (0.037M) of fuming nitric acid and 0.1 g (0.001M) of sulphuric acid are drop-wise added at a time under stirring. It is necessary to ensure a strict proportionality in the simultaneous addition of said reagents into acetic anhydride. Molar proportions of furfural diacetate, nitric acid, sulphuric acid and acetic anhydride are 1:1.5:0.041:5 respectively. Temperature of the reaction mixture is maintained within the range of from 0° to −10° C by means of external heat removal. The solution of furfural diacetate in acetic anhydride and the mixture of nitric and sulphuric acids are introduced into acetic anhydride at such rates as to maintain the nitration temperature at the above-mentioned predetermined value.

On completion of the addition, into acetic anhydride, of the total amount of the furfural diacetate solution and the mixture of nitric and sulphuric acids, the reaction mixture is stirred at a temperature within the range of from 0° to −10° C for an additional 20 minutes and then poured onto 20 g of crushed ice and stirred for 30 minutes, the reaction mixture being maintained at a temperature of from 10° to 15° C. These limits of the reaction mixture temperature are maintained by means of external heat removal. Thereafter, to the reaction mixture is added 5.9 ml of a 25% aqueous solution of caustic soda, under stirring, to bring a pH value to 3.5–4.5, the temperature of the reaction mixture being within the range of from 15 to 20° C. The reaction mixture, at said pH value, is heated to a temperature of from 50° to 55° C and maintained at this temperature for 1 hour under stirring. Then, to isolate the desired product, the reaction mixture is cooled to 10°–15° C and stirred at this temperature for 2 hours. The precipitated crystals of 5-nitrofurfural diacetate are treated by suction, washed with cold water and dried. The yield of 5-nitrofurfural diacetate was 5.3 g (85.6% of the theoretical value); melting point of the product was 91°–92° C.

Performing the nitration process in a manner similar to that described hereinbefore, but using different amounts of nitric acid, the following data illustrating yields and quality of 5-nitrofurfural diacetate were obtained. These are shown in Table 5 following hereafter.

Table 5

| Molar ratios of furfural diacetate, nitric acid and acetic anhydride | 5-nitrofurfural diacetate | |
|---|---|---|
| | Yield, % | Melting point, °C |
| 1:1.1:5 | 81.6 | 90 – 91.5 |
| 1:1.3:5 | 84.5 | 90 – 91.5 |
| 1:2.0:5 | 82.9 | 91 – 92 |

EXAMPLE 5

In this Example 5-nitrofurfural diacetate is prepared by performing the nitration process continuously. A laboratory unit for the production of 5-nitrofurfural diacetate is schematically shown in the accompanying drawing. In accordance with this drawing, the unit involves a nitration chamber 1 (50 ml capacity) provided with a dropping funnel 2 for a mixture of nitric and sulphuric acids, dropping funnel 3 for the solution of furfural in acetic anhydride, a thermometer 4 and a stirrer 5. The unit also includes a flask 6 (500 ml capacity) provided with a dropping funnel 7 for water, dropping funnel 8 for a 25% solution of caustic soda, thermometer 9 and a stirrer 10. Nitration chamber 1 and flask 6 are connected by means of a pipe 11 (length of about 150 mm, outside diameter of about 6 mm, inside diameter 3–4 mm), provided with a stopcock 12 and intended for a continuous discharge of the reaction mixture, by gravity, from chamber 1 into the flask 6. The nitration chamber 1 communicates with the outside atmosphere by means of a pipe 13 filled with anhydrous calcium chloride. The flask 6 communicates with the atmosphere by means of a pipe 14. The nitration chamber 1 is placed into a vessel 15 filled with a mixture of solid carbon dioxide and acetone, while flask 6 is placed into a vessel 16 filled with crushed ice.

Prior to the synthesis, the nitration chamber 1 is filled with 5–10 ml of acetic anhydride, flask 6 is filled with 10 ml of water, and dropping funnel 2 is filled with a mixture of 8.4 g (0.13M) fuming nitric acid and 0.37 g (0.0038M) of sulphuric acid. The dropping funnel 3 is filled with a solution of 9.6 g (0.1M) of furfural in 64.8 g (0.63M) of acetic anhydride, dropping funnel 7 is filled with water in the amount of about 60 ml and dropping funnel 8 is filled with about 25 ml of a 25% aqueous solution of caustic soda. Then stirrers 5 and 10 are switched on and acetic anhydride is cooled in the nitration chamber 1 to a temperature within the range of from −5 to −10° C; water in the flask 6 is cooled to a temperature within the range of from 0° to +5° C. Then, with the stirrers 5 and 10 operating and closed stopcock 12, the nitration chamber 1 is drop-wise filled with the simultaneously mixture of nitric and sulphuric acids from the dropping funnel 2 (at the supply rate of about 5.8ml/hr) and furfural solution in acetic anhydride from the dropping funnel 3 (at the supply rate of about 68 ml/hr). A strict proportionality should be ensured during the simultaneous addition of said components into the nitration chamber 1 (prevailing amount of the furfural solution added into the nitration chamber 1 is not allowed). Temperature of the reaction mixture in the nitration chamber 1 is maintained within the range of from 0° to −10° C by external heat removal effected by means of said cooling agent being present in vessel 15.

Continuous discharge of the reaction mixture from the nitration chamber 1 via pipe 11 into flask 6 is controlled by changing the position of stopcock 12 to ensure such a rate (about 74 ml/hr) that the initial liquid level (5–10 ml) in the nitration chamber 1 would remain constant.

The reaction mixture prepared in the nitration chamber 1 is then treated with water and neutralized with an alkali in said flask 6. To this end, into said flask the reaction mixture is added from the nitration chamber 1 through pipe 11 simultaneously with water from the dropping funnel 7 (at the supply rate of about 60 ml/hr) and a 25% solution of caustic soda from the dropping funnel 8 (at the supply rate of about 25 ml/hr). Temperature in flask 6 is maintained within the range of from 0° to −15° C by external cooling with ice placed into vessel 16.

After treatment with water and neutralization with an alkali, the reaction mixture with a pH value of from 4 to 5 is heated in the flask 6 to a temperature of from 50 to 55° C (to this end, ice in the vessel 16 is replaced with hot water) and maintained at this temperature for one hour under stirring. Then, to isolate the desired product, the reaction mixture is cooled to a temperature within the range of from 15° to 20° C, stirred at this temperature for 2 hours, and the resulting precipitating crystals of 5-nitrofurfural diacetate are treated by suction, washed with cold water and dried to give 18.6 g (76.3% of the theoretical value calculated on the amount of furfural introduced into the reaction) of 5-nitrofurfural diacetate. The melting point of the product is 90°-92° C.

EXAMPLE 6

Into a mixture of 6.4 g of acetic anhydride (0.0625M) at 10 ml of dichloromethane with a temperature of from 0° to −10° C, are simultaneously drop-wise added 2.40 g (0.025M) of furfural and a mixture of 2.02 g (0.032M) of fuming nitric acid and 0.09 g (0.0009M) of sulphuric acid. Molar proportions of furfural, nitric acid, sulphuric acid and acetic anhydride are 1:1.3:0.036:2.5 respectively. Temperature of the reaction mixture is maintained within the range of from 0° to −10° C by means of external heat removal. Furfural and the mixture of nitric and sulphuric acids are added into acetic anhydride at such rates as to maintain the nitration temperature at the above-mentioned predetermined level.

After addition, into the mixture of acetic anhydride with dichloromethane, of the total amount of furfural and the mixture of nitric and sulphuric acids, the reaction mixture is stirred at a temperature within the range of from 0° to −10° C for an additional 20 minutes. Then, to the reaction mixture is added 9 ml of cold water at a temperature of 2°-4° C and stirred for 20 minutes, while maintaining the reaction mixture at a temperature within the range of from 0° to 15° C by means of external heat removal. Thereafter, to the reaction mixture is added, under stirring, 2.0 ml of a 25% aqueous solution of caustic soda to bring a pH value to 3.5-4.5. Temperature of the reaction mixture is 10°-25° C. Thereafter, dichloromethane is distilled-off in vacuum by means of a water-jet pump (under a residual pressure of 15-25 mm Hg), the temperature being the water-bath of 20°-25° C. The reaction mass remaining after the removal of dichloromethane by distilling-off is washed with water till washings become colourless, whereafter there is added 8 ml of a 95% ethanol and 1.5 g of crystalline sodium acetate (which is added to maintain the pH value at the above-mentioned level). Then the reaction mixture is heated to a temperature of 45°-50° C and maintained at this temperature for 1 hour while stirring. Then, to isolate the desired product, to the reaction mixture is added 10 ml of cold water and stirred for 2 hours at a temperature within the range of from 15° to 20° C. The resulting crystalline residue is filtered-off, washed with 50 ml of cold water and dried at room temperature in a vacuum-desiccator over phosphorus pentoxide. The yield of 5-nitrofurfural diacetate is 4.72 g (77.8% of the theoretical value). The melting point of the product is 90° - 91° C.

Using tetrahydrofuran instead of a 95% ethanol solution, 5-nitrofurfural diacetate is obtained at the yield of 79.4% of the theoretical. The melting point of the product is 88° - 90° C.

EXAMPLE 7

Nitration of furfural, treatment of the resulting reaction mixture with water and alkali and isolation of the desired product are performed in a manner similar to that described in the foregoing Example 6. The only difference resides in that carbon tetrachloride is used instead of dichloromethane and isopropanol is used instead of a 95% ethanol. The yield of 5-nitrofurfural diacetate is 4.8 g (79.4% of the theoretical value). The melting point of the product is 88°-90° C.

EXAMPLE 8

Into a mixture of 7.7 g (0.075M) of acetic anhydride and 10 ml of dichloromethane having a temperature within the range of from 0° to +10° C are simultaneously drop-wise added 2.40 g (0.025M) of furfural and a mixture of 2.02 g (0.032M) of fuming nitric acid and 0.09 g (0.0009M) of sulphuric acid with stirring. Molar proportions of furfural, nitric acid, sulphuric acid and acetic anhydride are 1:1.3:0.036:3 respectively. Temperature of the reaction mixture is maintained within the range of from 0° to +10° C by means of external heat removal.

After addition, into the mixture of acetic anhydride and dichloromethane, of the total amount of furfural and the mixture of nitric and sulphuric acids, the reaction mixture is stirred for an additional 20 minutes at a temperature within the range of from 0° to 10° C. Then, to the reaction mixture is added 11 ml of cold water at a temperature of 2°-4° C and stirred for 20 minutes while maintaining the reaction mixture temperature within the range of from 0° to 15° C using external heat removal. Thereafter, the reaction mixture is slowly added, with stirring at the same temperature, to 3.1 ml of a 25% aqueous solution of caustic soda to bring a pH value to 3.5-4.5. Afterwards, to the reaction mixture is added 8 ml of acetone and heated under stirring and with a reflux condenser to a temperature of 50° - 55° C and maintained at this temperature for 1 hour. To isolate the desired product, the reaction mixture is cooled to a temperature within the range of from 15° to 20° C and stirred at this temperature for 2 hours. The solvent excess is distilled-off in vacuum created by means of a water-jet pump (residual pressure 15-25 mm Hg), the temperature of the water bath being 20°-25° C. The resulting crystalline residue is filtered-off, washed with 50 ml of cold water and dried to give 4.8 g (79.4% of the theoretical value) of 5-nitrofurfural diacetate melting at 89° - 91° C.

What is claimed is:

1. A method of preparing 5-nitrofurfural diacetate comprising nitrating a compound selected from the group consisting of furfural and furfural diacetate at a temperature ranging from −10° to +10° C; said nitrating being effected by gradually, simultaneously, and separately adding said compound and a mixture of nitric and sulphuric acids into acetic anhydride having a temperature ranging from −10° to +10° C with constant stirring of the resulting reaction mixture; molar ratios of the compound being nitrated, nitric and sulphuric acids being maintained equal to 1:1.1-2:0.036-0.041, respectively; said compound and the mixture of acids being added into the acetic anhydride at such rates as to maintain the nitrating reaction temperature at a predetermined level; said furfural diacetate, when used as the compound being nitrated, being employed in the form of its solution in acetic anhydride; treating the reaction mixture resulting from the nitration with water at a temperature ranging from 0° to 15° C at a weight ratio between water and the starting acetic anhydride of from 1.1:1 to 1.8:1, respectively, and neutralizing it with an alkali to a pH of 3.5-5 at a temperature of from 0° to 25° C, then maintaining the reaction mixture at a pH within said range at a temperature of from 45° to 55° C, and thereafter isolating the desired product from the reaction mixture.

2. A method as claimed in claim 1, wherein the nitration is effected at a molar ratio between the compound being nitrated and acetic anhydride equal to 1:2.5-6.3 respectively.

3. A method as claimed in claim 1, wherein furfural is added, into acetic anhydride, as its solution in acetic anhydride.

4. A method as claimed in claim 1, wherein the compound being nitrated and the mixture of nitric and sulphuric acids are added into a mixture of acetic anhydride with an inert organic chlorinated solvent at a volumetric ratio between acetic anhydride to said solvent ranging from 1:1.4 to 1:2, respectively, and after neutralization of the reaction mixture with an alkali prior to maintaining it at a temperature within the range of from 45° to 55° C, said reaction mixture is mixed with a water-miscible organic solvent.

5. A method as claimed in claim 4, wherein prior to the addition of the water-miscible organic solvent to the reaction mixture, the inert chlorinated organic solvent is distilled off.

6. A method as claimed in claim 4, wherein the inert organic chlorinated solvent is selected from the group consisting of dichloromethane and carbon tetrachloride and the water-miscible organic solvent is selected from the group consisting of ethanol, isopropanol, tetrahydrofuran and acetone.

7. In the method of preparing 5-nitrofurfural diacetate by nitrating a compound selected from the group consisting of furfural and furfural diacetate with a nitrating agent to produce a nitrated intermediate and thereafter converting the nitrated intermediate into 5-nitrofurfural diacetate, the improvement which comprises nitrating the compound to prepare the nitrated intermediate by gradually, simultaneously, and separately adding the compound and a mixture of nitric acid and sulfuric acid into acetic anhydride at a temperature of −10° to +10° C and at such rates so as to maintain this temperature, with constant stirring of the reaction mixture, the addition of said compound, nitric acid, and sulfuric acid being maintained in the molar ratios of 1:1.1-2:0.036-0.041, respectively.

8. The method of claim 7 wherein the compound is furfuryl diacetate and it is employed in the form of its solution in acetic anhydride.

9. The method of claim 7 wherein the compound and the mixture of nitric and sulphuric acids are added into a mixture of acetic anhydride and an inert organic chlorinated solvent at a volumetric ratio of acetic anhydride to said solvent ranging from 1:1.4 to 1:2, respectively.

* * * * *